United States Patent [19]

Hsieh

[11] Patent Number: 5,731,303
[45] Date of Patent: Mar. 24, 1998

[54] TRANSDERMAL AND TRANS-MEMBRANE DELIVERY COMPOSITIONS

[75] Inventor: Dean Hsieh, Brandamore, Pa.

[73] Assignee: Conrex Pharmaceutical Corporation, Phoenixville, Pa.

[21] Appl. No.: 361,833

[22] Filed: Dec. 22, 1994

Related U.S. Application Data

[63] Continuation-in-part of Ser. No. 270,807, Jul. 5, 1994, abandoned, which is a continuation of Ser. No. 713,423, Jun. 10, 1991, abandoned, which is a continuation of Ser. No. 449,117, Dec. 8, 1989, Pat. No. 5,023,252, which is a continuation of Ser. No. 138,830, Dec. 28, 1987, abandoned, which is a continuation-in-part of Ser. No. 899,049, Aug. 21, 1986, abandoned, which is a continuation-in-part of Ser. No. 804,661, Dec. 4, 1985, abandoned.

[51] Int. Cl.$^6$ ........................................ A61K 31/55
[52] U.S. Cl. .................. 514/183; 514/431; 514/449; 514/450; 514/906; 514/947

[58] Field of Search ........................ 514/183, 431, 514/450, 449, 946, 947

[56] References Cited

U.S. PATENT DOCUMENTS 5,023,252  6/1991  Hseih ........................... 514/183

*Primary Examiner*—John W. Rollins
*Attorney, Agent, or Firm*—Synnestvedt & Lechner

[57] ABSTRACT

The rate of absorption of drugs across skin and other body membranes such as mucous membranes and the blood brain barrier is enhanced by adding to the drug composition a compound which enhances the rate. This compound may be a macrocyclic ester, diester, amide, diamide, amidine, diamidine, thioester, dithioester, thioamide, ketone or lactone. The macrocyclic ketone contains at least 12 carbon atoms.

7 Claims, No Drawings

TRANSDERMAL AND TRANS-MEMBRANE DELIVERY COMPOSITIONS

CROSS-REFERENCE TO RELATED APPLICATIONS

This is a continuation-in-part of U.S. Ser. No. 08/270,807, filed Jul. 5, 1994 (now abandoned), which is a continuation of U.S. Ser. No. 07/713,423, filed Jun. 10, 1991 (now abandoned), which is a continuation of U.S. Ser. No. 07/449,117, filed Dec. 8, 1989 (now U.S. Pat. No. 5,023,252), which is a continuation of U.S. Ser. No. 07/138,830, filed Dec. 28, 1987 (now abandoned), which is a continuation-in-part of U.S. Ser. No. 06/899,049, filed Aug. 21, 1986 (now abandoned), which is a continuation-in-part of U.S. Ser. No. 06/804,661, filed Dec. 4, 1985 (now abandoned).

FIELD OF THE INVENTION AND REPORTED DEVELOPMENTS

This invention relates to transdermal and transmembrane delivery of physiologically active agents such as drugs to humans and animals. It particularly relates to systems for delivering of drugs across skin, membranes of various body cavities such as ocular, nasal, oral, buccal, anal, rectal, vaginal, and blood brain barrier and like membranes, and providing an enhanced rate of passage across such skin or membranes. This invention relates also to a composition which is effective in improving a physiologic condition of the body.

Naturally, body membranes of all sorts represent protective barriers against foreign materials and infection. However, administration of drugs using transdermal and transmembrane delivery systems does provide improved therapeutic advantages and better patient compliances which is well known and documented in both the patent and scientific literature. Examples of such systems are disclosed in U.S. Pat. Nos. 3,921,636; 3,964,482; 3,989,816; 3,996,934; 4,201,211; 4,291,014; 4,291,015; 4,292,203; 4,336,243; 4,346,709; 4,379,454; 4,409,206; 4,460,372; 4,486,193; and 4,490,322.

Administration using transdermal and trans-membrane drug delivery systems has certain advantages over the conventional methods of oral and systemic administration. These advantages include: (1) minimizing drug exposure by allowing a significant reduction in dosage; (2) providing long-term therapy in a single dose thereby increasing patient compliance; (3) avoiding the risks and inconveniences of intravenous or intramuscular therapy; (4) rendering possible the use of drugs with short biological half-lives; (5) allowing immediate termination of drug input by simply removing the material containing the drug; and (6) avoiding the possible inactivation of a drug when it first passes through the liver after oral administration.

Examples of drugs which have been administered transdermally include scopolamine, nitroglycerine, clonidine, estradiol, antibiotics (e.g., erythromycin, lincomycin, and the like), antifungal agents, and sunscreens. Many of these drugs, e.g., clonidine, scopolamine, and nitroglycerine are of such chemical structure that they can permeate the skin and other body membranes to provide sufficiently high therapeutic doses for most purposes. However, when higher therapeutic levels are required, or when the drug itself, e.g., estradiol diacetate, does not permeate or cannot sufficiently permeate the skin to provide the desired level of drug concentration, it becomes necessary to use adjuvants which enhance the rate of penetration of the drug. Generally, for transdermal formulation of most drug entities adjuvants are required.

TRANSMEMBRANE DELIVERY OF DRUGS

Besides skin, mucous membranes cover the surface area of various body cavities such as nasal, oral, buccal, anal, rectal, and vaginal, which protect the body from the invasion of foreign materials. These membranes represent alternative routes of drug administration; in particular, for such drugs as peptides and proteins or other macromolecules (generally speaking, molecular weight larger than 1,000 daltons produced by genetic engineering or biotechnology). An example of trans-nasal delivery of insulin, molecular weight of 6,500 daltons, enhanced by surfactant in rats was reported by Hirai, Yashiki and Mima in the International Journal of Pharmaceutics, Vol. 9, pages 165-172, 1981 and International Journal of Pharmaceutics, Vol 9, pages 173-184, 1981. Further studies in human subjects (using insulinbile salt aerosol) were reported by Moses, Gordon, Carey, and Flier in Diabetes Vol. 32, pages 1040-1047, 1983. Nasal spray of insulin could possibly eliminate the need of subcutaneous insulin injection by diabetics and better patient compliances could possibly be achieved.

The uses of proteins, peptides, enzymes, nucleic acids, lipids, and complexes of thereof, as therapeutic agents have been documented. Oral administration is not suitable in most cases, as such drugs are destroyed in the digestive tract. Subdermal injections and implantation have inherent disadvantages, such as discomfort of administration, the necessity for administration by trained personnel, and problems with patient compliance. Transdermal administration has technical difficulties which was reviewed by Dean Hsieh in the chapter on Devices for Macro-molecules, pages 171-193, Transdermal Delivery of Drugs, Volume I, edited by Agis F. Kydonieus and Bret Berner, published by CRC Press. Therefore, with suitable penetration enhancers, transmembrane delivery of such macromolecules is an alternative route of choice for drug administration.

DELIVERY OF DRUGS THROUGH BLOOD-BRAIN BARRIER

The brain is surrounded by an endothelial capillary wall commonly known as the blood-brain barrier. This barrier is effective in protecting the brain from potentially harmful chemicals, but renders the administration of potentially beneficial drugs to the afflicted brain difficult, if not impossible, when the brain suffers from infection, tumor, or disfunction. Bodor and Farag reported a chemical redox drug delivery system to transmit drugs through blood-brain barrier. (See Bodor, H. and Farag, H. H., "Improved Delivery through Biological Membranes XIV: Brain-specific, Sustained Delivery of Testosterone Using a Redox Chemical Delivery System", in the Journal of Pharmaceutical Science, Vol. 73 (3), pages 385-388, 1984.) Drugs are bonded to a quarternary salt which is chemically reduced to a lipoidal dihydropyridine carrier. Upon administration, the compound is distributed throughout the body. The lipid-water partition ratio of the carrier allows it to deliver the drug to the brain. The compound is oxidized in vivo and reverts to its original form. The ionic, hydrophilic salt is quickly eliminated from the body, except that the blood-brain barrier (which works both ways) prevents its elimination from the brain. Enzymes remove the drug from the carrier, providing sustained release of drugs to the brain. No permeation enhancers were used in Bodor's work.

Compounds which have been used as adjuvants include dimethyl sulfoxide and homologs thereof, 1-alkyl-azacycloheptan-2-ones (azone), N,N-dimethyl-m-toluidine, long chain aliphatic alkanes, alcohols, carboxylic acids and esters and substituted (e.g., halo) derivatives thereof, cyclohexyalkanols, phenylalkanols, mixtures of siloxanes with either amides or urea derivatives, $C_{3-4}$ diols and ethers and esters thereof, mixtures of $C_{3-4}$ diols with surfactants, eucalyptol, urea, a mixture of 2-pyrrolidone and dimethyl formamide, 1,3-dimethyl-2-imidazolidinone, dicyclohexylmethylamine oxide, a mixture of hexane and ethylene glycol monomethyl ether, a mixture of ricinoleyl alcohol and an ethoxylated partial glycerine of a $C_{6-12}$ saturated fatty acid, N-substituted-diisopropylamines, and compounds of the formula

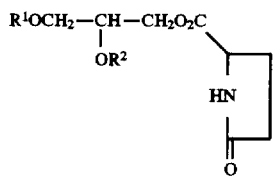

wherein $R^1$ and $R^2$ are hydrogen, $C_{1-25}$ alkyl, $C_{2-25}$ alkenyl, $C_{1-24}$ alkyl carbonyl, or $C_{2-24}$ alkenyl carbonyl.

While all of the above-listed adjuvants do serve to enhance the transdermal absorption of drugs, they possess certain drawbacks in that (i) some are regarded as toxic (e.g., dimethyl sulfoxide); (ii) some irritate the skin (e.g., surfactants); (iii) some on prolonged use have a thinning effect on the skin (e.g., oleic acid); and (iv) some change the intactness of the skin structure, resulting in a change in the diffusability of the drug (e.g., azone).

U.S. Pat. Nos. 3,921,636; 3,964,482 and 3,996,934 mention that cyclic ketones containing from 4 to 10 carbon atoms serve to enhance the transdermal absorption of drugs; however, no specific showing of such enhancement, or for that matter any transdermal absorption in the presence of such ketones, is shown.

Furthermore, my studies have demonstrated that there is little or no enhancement using cyclic ketones containing from 9 to 11 carbon atoms.

OBJECTS OF THE INVENTION

It is, accordingly, an object of this invention to provide a method for enhancing the rate of passage of drugs across skin, membranes of various body cavities, blood-brain barrier and like membranes.

It is another object of this invention to provide drug containing compositions which have an enhanced rate of passage across skin, membranes of various body cavities, blood-brain barrier and like membranes.

It is a further object of the invention to provide adjuvants or permeation enhancers which when added to drug compositions enhance the rate passage of the drug therein across skin, membranes of various body cavities, blood-brain barrier and like membranes.

It is still another object of this invention to provide adjuvants or permeation enhancers which are non-toxic and do not exert any physiological effects in the body other than enhancing the rate of passage of-drugs across skin, membranes of various body cavities, blood-brain barrier and like membranes.

It is still another object of this invention to provide adjuvants or permeation enhancers which have a minimal effect on the structure of the skin, membranes of various body cavities, blood-brain barrier and like membranes.

It is a further another object of this invention to provide adjuvants or permeation enhancers which are compatible with drugs, pharmaceutical vehicles, and polymers.

SUMMARY OF THE INVENTION

In accordance with this invention, it has been found that the addition to a composition containing an effective amount of a drug and a compound of the structure;

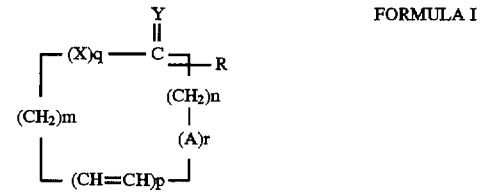

FORMULA I wherein X and Y are oxygen, sulfur or an imino group of the structure =N—R with the proviso that when Y is the imino, group X is an imino group and when Y is sulfur X is sulfur or an imino group, A is a group having the structure

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and R is hydrogen or an alkyl group having from 1 to 6 carbon atoms and may be straight chained or branched, with the proviso that when p, q and r have a value of 0 and Y is oxygen, m+n is at least 11, will enhance the rate of the passage of the drug across body membranes. Hereinafter these compounds are referred to as enhancers.

When R is alkyl it may be methyl, ethyl, propyl, isopropyl, butyl, isobutyl, sec-butyl, amyl, hexyl, and the like.

DETAILED DESCRIPTION OF THE INVENTION

In practicing this invention the enhancer is dissolved, dispersed, suspended, or solubilized in suitable solvent(s) such as alcohols, oils, glycerol, ethylene glycol, propylene glycol, hexane, acetone, freon, water, other polar or non-polar solvents, or their mixture thereof, which is then added to a composition comprising an effective amount of the desired drug admixed with a pharmaceutical carrier in an amount so that the concentration of the enhancer in the composition comprising the drug, pharmaceutical carrier and enhancer solution will be from about 0.1% to about 50% by weight. Preferably, the concentration of the enhancer will be from about 0.1% to about 30% by weight. In some cases., when the enhancers are in the liquid form a "neat" solution of enhancer can be directly incorporated in the drug, pharmaceutical carrier, and enhancer mixture, in which the concentration of enhancer ranges from 0.1% to about 30% by weight.

Pharmaceutical carriers include suitable non-toxic vehicles in which the drug is dissolved, dispersed, impregnated, or suspended, such as solvents, fatty materials, celluloses and their derivatives, proteins and their derivatives, collagens, gelatine, polymers, adhesives, sponges, fabrics, and the like and adjuvants which are added to provide better solubility or dispersion of the drug in the vehicle. Such adjuvants may include non-toxic surfactants, solubilizers, emulsifiers, chelating agents, binding materials, lubricants softening agents, and the like.

Preferably, the compounds of this invention are the cyclic lactones (the compounds wherein both X and Y are oxygen, (q is 1 and r is 0), the cyclic diesters (the compounds wherein both X and Y are oxygen, and both q and r are 1), and the cyclic ketones (the compounds wherein both q and r are 0 and Y is oxygen). In the cyclic diesters m+n is preferably at least 3. In the cyclic ketones, m+n is preferably from 11 to 15 and p is preferably 0.

The drug composition, which may be administered topically, nasally, buccally, aurally, rectally, ocularly, orally, vaginally, or through the navel, may be in the form of solutions, creams, sprays, lotions, aerosols, suppositories or jellies; or incorporated in patches, films, tapes or bandages.

The invention will become clearer from the examples which follow. These examples represent preferred embodiments of the invention and are not to be regarded as limiting.

The evaluations of the composition of this invention in enhancing the rake of permeation of the drug were performed at various sites of the body. These sites included skin, mucous membranes of various body cavities, and blood-brain barrier.

The evaluation of the compositions of this invention in enhancing the rate of penetration of the drug through the skin was carried out in vitro using skin preparations obtained from homozygous Hr/Hr hairless mice (HRS/J) strain following the procedures described by Chow, Kaka and Wang in the J. Pharmaceut. Sci. 73 (12) 1794–1799 (1984) for the preparation, study and data analysis.

Animals between 2 to 4 months of age were selected. In all selected animals, the skins were grossly normal and free of bites, scratches or bruises. The mice were killed by $CO_2$ inhalation, and the skin was removed. The full-thickness skin was used in the penetration studies.

The skin preparation was mounted between the donor and receptor chambers of a Franz diffusion cell. The stratum corneum (SC) was exposed to the ambient condition and the dermal side was oriented toward a pH 7.4 saline-phosphate buffer, simulating the physiological pH of 7.3–7.4 of the dermal side, in the receptor chamber.

The solution of the receptor chamber was equilibrated by circulating water at 32° C. through a jacket surrounding the chamber, which temperature was chosen to reflect the temperature of the SC, prior to the applications of the test sample. Mixing of the solution in the receptor chamber was accomplished by magnetic stirring.

A known amount of a radioisotope-labeled drug, diluted with non-radioactive (cold) drug, with or without the adjuvant, was applied so as to spread across the SC surface of the mounted skin. Aliquots of the saline-phosphate buffer containing any radioisotope labeled drug which had penetrated through the skin into the receptor chamber were withdrawn from the side arm of the receptor chamber, and a volume of fresh saline-phosphate buffer equal to the volume of the withdrawn aliquot was added to the receptor chamber. Aliquots were withdrawn every thirty minutes during the first 2 hours and every hour during the next 10 hours, the total time of the study thus lasting up to 12 hours. The amount of the drug which had passed through the skin was measured by liquid scintillation counting of the withdrawn aliquot in Aquasol-2.

Penetration profiles of the drugs were constructed by plotting the amount of the drug which had penetrated the skin versus time. Profiles for control samples (no adjuvant added) and for tested samples (containing an adjuvant) were plotted for purposes of comparison.

The permeability parameters which are shown in the tables were calculated in accordance with the method of Chow, Kaka and Wang as described on page 1795 of their paper.

EXAMPLE 1

To a propylene glycol solution containing $4.74 \times 10^{-2}$ mg/ml of tritiated triaminolone acetonide 2% w/v of the adjuvant was added. The adjuvants tested were 3-methylcyclopentadecanone (I), cyclopentadecanone (II), cycloundecanone (III), and cyclododecanone (IV). Each of these cyclic ketones is commercially available. The preparations were tested according to the method described above.

The total amount of tritiated triamcinolone acetonide and the rates of penetration (flux) calculated from the linear portion of the curve are shown in Table 1.

TABLE 1

| Adjuvant | Flux | | Total Amount* | |
|---|---|---|---|---|
| | $X10^3 dpm/cm^2/hr$ | Ratio % | $dpm(X10^3)$ | Ratio % |
| Control | 0.16 | 100 | 1 | 100 |
| I | 0.70 | 437 | 3.5 | 350 |
| II | 1.07 | 669 | 4.8 | 480 |
| III | 0.25 | 156 | 1.5 | 150 |
| IV | 0.25 | 156 | 1.7 | 170 |

*Total amount of triamincinolone acetonide which penetrated at the end of 10 hours.

EXAMPLE 2

Nasal Absorption of Insulin in Dogs

The object of this study was to demonstrate that nasal absorption of therapeutic proteins, peptides, carbohydrates, nucleic acids, lipoproteins, mucoproteins, lipoproteins, and other macromolecules in living animals and humans can be achieved with the addition of skin enhancers such as cyclopentadecanolide.

Beagle dogs weighing 10 to 12 kg were used in this study. The formulation of the nasal spray was composed of Freon, insulin, and cyclopentadecanolide packaged in a metered nasal spray device which is commercially available. Before applying nasal spray in dogs, the dogs were anaesthesized using Nembutal (or pentabarbitol) at the dose of 40–50 mg/kg. Fifteen minutes before application, blood samples were obtained. The nasal spray of insulin was then applied with the aid of applicator. Blood samples were again obtained at 0, 10, 20, 30, 45, 50, 90, 120 and 180 minutes. Both blood glucose determined by YSI glucose analyzer and serum insulin levels determined by radioimmunoassay were tested. Both methods were commonly practiced in the laboratory.

Table 2 shows the blood glucose and serum insulin levels of dogs receiving insulin nasal spray containing cyclopentadecanolide. Obviously, when nasal spray of insulin with cyclopentadecanolide was applied (sprayed) in the nasal cavity of dogs, serum insulin levels abruptly increased to 71.2 uU/ml in 10 minutes and maintained the level for about 30 minutes, then gradually decreased and levelled off in 3 hours. On the other hand, blood glucose levels decreased from 83.6 mg/dl at 0 minute to 51.5 mg/dl at 30 minutes as serum insulin levels increased from 2.7 uU/ml at 0 minute to 67.1 uU/ml at 30 minutes. Then, the blood glucose levels maintained almost constant for about 80 minutes. Finally, when serum insulin was depleting at 120 minutes to 7.9 uU/ml at 180 minutes, blood glucose levels rose from 45.8 mg/dl to 72.7 mg/dl within the same time span.

TABLE 2

Nasal Absorption of Insulin in Dogs with Cyclopentadecanolide

| Time (minutes) | Blood Glucose (mg/dl) | Serum Insulin (uU/ml) |
|---|---|---|
| −15 | 81.0 ± 3.2 | 1.7 ± 0.6 |
| 0 | 83.6 ± 1.6 | 2.7 ± 1.3 |
| 10 | 80.7 ± 2.7 | 71.2 ± 28.3 |
| 20 | 68.4 ± 9.1 | 78.6 ± 26.6 |
| 30 | 51.5 ± 9.5 | 67.1 ± 23.9 |
| 45 | 35.2 ± 6.6 | 53.3 ± 13.6 |
| 60 | 40.1 ± 5.3 | 40.7 ± 10.9 |
| 90 | 38.7 ± 0.4 | 14.2 ± 3.9 |
| 120 | 45.8 ± 3.0 | 10.8 ± 2.7 |
| 180 | 72.7 ± 8.3 | 7.9 ± 2.8 |

1. Three dogs were used in the study
2. Data were expressed as mean ± S.E.M.
3. The dose of insulin used in each dog was 1 U/kg body weight
4. The concentration of cyclopentadecanolide in Freon solution was 1%

Control experiments included the following:

(1) Placebo without insulin but containing skin enhancer, (2) Phosphate buffer solution, and (3) insulin itself. When these control formulations were sprayed in the nasal cavity in dogs, no changes in both blood glucose level and serum insulin were found.

Example 2 illustrates the use of macrocyclic compounds in the nasal spray of insulin formulations for diabetes treatment. The practice of this invention as a spray is not limited to insulin alone, but is suitable for many therapeutic proteins and peptides. To name a few, interferon for common colds, cancer, and viral infection, lymphokines for cancer and immunity disease, growth hormones for dwarfism, luteinizing hormone releasing hormones (LHRH) analogs for birth control, enkaphaline for pain relief, and so on.

EXAMPLE 3

Nasal Insulin Spray for the Treatment of Diabetics

The objective of this study is to evaluate the efficacy of a nasal insulin spray containing macrocyclic compounds as permeation enhancers for diabetic treatment. The methodology of this study follows the methods published by two different groups of scientists. One was by Alan C. Moses, Gilad S. Gordon, Martin C. Carey, and Jeffrey S. Flier in Diabetes Vol. 32, p. 1040–1047, 1983, Insulin Administered Intranasally as an Insulin-Bile Salt Aerosol. The other was by Antonio E. Pontiroli, Miriam Alberetto, Antonio Secci, Giorgio Dossi, Isabella Bosi, and Guido Pozza, in British Medical Journal Vol 284, p. 303–306, 1982. Insulin given Intranasally Induced Hypoglycemia in Normal and Diabetic Subjects.

The enhancer used in this study is 1% cyclopentadecanolide and insulin used is U-200 porcine insulin. The tested subjects receive 4 sprays of enhancer solution (two sprays each nostril), then 2 sprays U-200 (1 spray each nostril) or equivalent to 40 U per 60 kilograms. Before spraying, the subjects would fast for two hours. The subjects were asked to take a deep breath when nasal insulin spray was administered.

Blood samples were drawn 20 minutes before insulin administration. After spraying, blood samples were drawn every 30 minutes. Blood glucose levels were determined using radioimmuniassay.

Four subjects who have hyperglycemia history were selected to receive nasal insulin sprays. Two other subjects as a control group receiving either enhancer or insulin only.

The results obtained from four Type II diabetics are shown in Table 3. They clearly indicated that blood glucose levels can be decreased by receiving nasal insulin spray. In other words, insulin can be absorbed through nasal membrane when cyclopentadecanolide is incorporated into the formulation. This was further confirmed by the determination of serum insulin levels form the same blood samples. For the one who received enhancer spray only, the blood glucose levels did not decrease. Neither did it for the one who received insulin solution without enhancer.

TABLE 3

| Blood glucose measurement of diabetics receiving nasal insulin spray. | | | | |
|---|---|---|---|---|
| Time | Subject 1 | Subject 2 | Subject 3 | Subject 4 |
| 20 min. | <400 mg/dl | 276 mg/dl | 384 mg/dl | 308 mg/dl |
| 30 min | 399 | 246 | 334 | 277 |
| 60 min | 388 | 209 | 325 | 274 |
| 90 min | 342 | — | — | 266 |
| 120 min. | 339 | — | 279 | 244 |

1. Insulin solution is U-200 porcine insulin.
2. Permeation enhancer used is 1% cyclopentadecanolide in Freon.
3. Four subjects were Type II diabetics.
4. "−20 min" indicates that blood samples were taken 20 minutes before nasal spray.

EXAMPLE 4

Vaginal Sponge for Estrus Synchronization in Sheep.

The objective of this study was to demonstrate the vaginal absorption of therapeutic agents can be achieved to desirable therapeutic levels by the addition of permeation enhancers such as cyclopentadecanolide. Polymer sponges made of polyurethane or the like were impregnated with 80% fluorogestorone acetate and 20% cyclopentadecanolide. The sponge was inserted into the vagina of ewes for up to 12 days. Blood samples were drawn and the levels of fluorogestorone acetate were determined by radioimmunoassay. Table 4 shows the blood levels of fluorogestorone acetate in ewes during the time course of treatment. The later phase of treatment is the decisive indicator for estrus synchronization in ewes. The results clearly indicated that at the later phase off treatment (i.e., days 6, 9, and 12), the blood levels in those ewes receiving sponges containing permeation enhancers such as cyclopentadecanolide are higher than those without permeation enhancers.

TABLE 4

| Blood levels of Fluorogestorone Acetate in Ewes | | | | | | | |
|---|---|---|---|---|---|---|---|
| Treatment and | | Day of Treatment | | | | | |
| Animal No. | | 0 | 3 | 6 | 9 | 12 | 13 |
| | | (Nanogram/ml) | | | | | |
| -ve Control | 1 | 3.61 | 0.19 | 0.47 | 0.22 | 0.20 | 0.34 |
| | 2 | 6.82 | 0.48 | 0.39 | 0.25 | 0.19 | 0.23 |
| | 3 | 0.69 | 0.36 | 0.36 | 0.07 | 0.09 | 0.32 |
| | X | 3.70 | 0.34 | 0.41 | 0.18 | 0.16 | 0.30 |
| | SED | 1.77 | 0.08 | 0.03 | 0.05 | 0.03 | 0.03 |
| Sponge I | 4 | 0.56 | 2.61 | 1.42 | 2.05 | 1.11 | 0.39 |
| (No Enhancer) | 5 | 3.15 | 3.23 | 2.26 | 1.49 | 1.56 | 0.19 |
| | 6 | 5.51 | 3.26 | 3.61 | 2.53 | 2.41 | 0.43 |
| | 7 | 0.80 | 2.06 | 1.39 | 2.05 | 1.47 | 0.22 |
| | X | 2.51 | 2.79 | 2.17 | 2.03 | 1.64 | 0.31 |

TABLE 4-continued Blood levels of Fluorogestorone Acetate in Ewes

| Treatment and Animal No. | | Day of Treatment | | | | | |
|---|---|---|---|---|---|---|---|
| | | 0 | 3 | 6 | 9 | 12 | 13 |
| | SED | 1.16 | 0.28 | 0.52 | 0.21 | 0.28 | 0.06 |
| Sponge II | 8 | 2.62 | 2.12 | 2.06 | 3.61 | 2.51 | 0.34 |
| (With Enhancer) | 9 | 0.87 | 4.27 | 2.53 | 2.31 | 2.13 | 0.41 |
| | 10 | 0.82 | 3.33 | 2.18 | 2.39 | 2.04 | 0.59 |
| | 11 | 1.06 | 2.02 | 2.22 | 2.81 | 2.24 | 0.63 |
| | X | 1.34 | 2.94 | 2.56 | 2.78 | 2.23 | 0.49 |
| | SED | 0.43 | 0.54 | 0.10 | 0.30 | 0.10 | 0.07 |

Blood-Brain Barrier and Central Nervous Systems

The blood-brain barrier (BBB) is comprised of brain microvessel endothelial cells characterized by tight intercellular junctions, minimal pinocytic activity, and the absence of fenestra. These characteristics endow microvellel endothelial cells with ability to restrict passage of most small polar blood-borne molecules (e.g. neurotransmitter catecholamines, small peptides and macromolecules, e.g. proteins) from the cerebrovascular circulation to the brain. On the other hand, within the cerebrovasculature, the blood-brain barrier is a dynamic regulatory interface that poses a formidable barrier to delivery of pharmacological modalities to the central nervous system.

EXAMPLE 5

The objective of this study is to demonstrate the use of a blue dye as a marker penetrable into central nervous system (e.g. brain) with the addition of cyclopentadeconaolide in the infusion solution. One gram of cyclopentadecanolide was first dissolved in 0.5 ml absolute alcohol solution. The solution was then mixed with 10 ml of physiological saline-dye solution. The mixture was then filtered through a Millipore filter to remove excess amount of cyclopentadecanolide and thus a saturated cyclopentadecanolide solution was made for infusion. Three ml of the above solution was infused into the carotid artery of anethesized rats weighing about 250 grams. Cautions were taken to ensure that the infusion solution was entered into one side of the brain by clamping the other veins and arteries with surgical clips. The other side of the brain was used as a contrast. It was observed that the the tested side of the brain and the eye in the rat were deep blue in color due to the penetration of the blue dye enhanced by the use of cyclopentadecanolide; while the other side remained normal in color. It was observed also that the sections of the brain exhibit a deep blue color on the left or tested side; while the right or contrast side appears normal in color. The test results indicated that the addition of cyclopentadecanolide to the infusion solution effects the penetration of chemicals through the blood brain barrier in rats.

Types of Macrocyclic Compound as Permeation Enhancer

Studies were performed to demonstrate that (1) the macrocyclic ketones containing more than 11 carbons possess unexpected desirable properties which are not possessed by those ketones having lower carbon content; (2) additional macrocyclic ketones such as e.g. muscone which has an alkyl group in the macrocyclic ring have similar enhancing properties; (3) other macrocyclic compounds such as cyclopentadecanolide which have an additional oxygen in the macrocyclic ring possess enhancing properties; (4) Another macrocyclic compound such as civetone which have unsaturated bond in the macrocyclic ring possess enhancing properties: (5) Other macrocyclic compounds such as ethylene brassylate which is the polyester of long chain dicarboxylic acid and ethylene glycol possess enhancing properties.

EXAMPLE 6

Comparison of different cyclic ketones for the enhancement of percutaneous absorption of drugs through hairless mouse skin.

In this study, six different cyclic ketones were used for comparative studies on the percutaneous absorption of tritiated hydrocortisones through hairless mouse skin. These include cyclononanone (C9), cyclodecanone (C10), cycloundecanone (C11), cyclododecanone (C12), cyclotridecanone (C13), and cyclopentadecanone (C15). The preparation, penetration study, and data analysis of the experiment followed the procedure referred to in Example 1. For each compound, five skin samples were used for percutaneous absorption study. The concentration of enhancers used in the donor compartment was 2%. The duration of the experiment was performed for 10 hours when the steady-rate of penetration of drugs has been reached for at least several hours. The test data was graphed to show the penetration profiles of hydrocortisone from percutaneous absorption enhanced by the different cyclic ketones through hairless mouse skin. The ranking of the potency of the enhanced absorption property of different cyclic ketones are in the following order: cylclopentadecanone>cyclotridecanone>cyclododecanone>cyclononanone>cycloundecanone>cyclodecanone (a decreasing order). The slope of the penetration profiles, which represent the steady state permeation rate of drugs, were calculated and shown in Table 5. The enhancement factor of different cyclic ketones was calculated based upon the control group as 100. There was a slight decrease in the permeation rate of hydrocortisone through hairless mouse skin when cyclodecanone and cycloundecanone were used as skin enhancers respectively. In other words, both cyclodecanone and cycloundecanone slightly inhibit the percutaneous absorption of hydrocortisone through hairless mouse skin. There was a little effect in the percutaneous absorption of hydrocortisone through hairless mouse skin when cyclononanone was used. There was a 230% increase in the permeation rate of hydrocortisone through hairless mouse skin when cyclododecanone was used in the study. However, there was a 524% increase and a 590% increase in percutaneous absorption of hydrocortisone through hairless mouse skin when cyclotridecanone and cyclopentadecanone were used as skin enhancers respectively. Additionally cyclopentadecanolide, a macrocyclic compound having an oxygen atom in the macrocyclic ring, was used in the same study for comparison. There was a 17-fold increase in percutaneous permeation rate of hydrocortisone through hairless mouse skin.

From this study, it was clearly demonstrated that (1) the cyclic ketones containing more than 11 carbon atoms possess unexpected, desirable properties which re not possessed by those ketones having a lower carbon content, (2) the higher the carbon number in the macrocyclic ring, the higher the enhanced permeation rate of hydrocortisone through hairless mouse skin.

TABLE 5

Comparison of permeation rate of hydrocortisone through hairless mouse skin by different cyclic ketones

| Chemical(s) | Permeation Rate (ug/cm*cm/hr) | Enhancement factor (%) |
|---|---|---|
| None or control | $5.25 \times 10^{-5}$ | 100 |
| cyclononanone | $5.96 \times 10^{-5}$ | 113 |
| cyclodecanone | $3.79 \times 10^{-5}$ | 72 |
| cycloundecanone | $3.91 \times 10^{-5}$ | 74 |
| cyclododecanone | $1.21 \times 10^{-4}$ | 230 |
| cyclotridecanone | $2.75 \times 10^{-4}$ | 524 |
| cyclopentadecanone | $3.10 \times 10^{-4}$ | 590 |
| cyclopentadecanolide | $8.94 \times 10^{-4}$ | 1703 |

1. The concentration of chemical used in the donor compartment was 2%.
2. Permeation rates were calculated from the slope of permeation profile.
3. The enhancement factor was calculated based upon the control group (without chemical) as 100.

EXAMPLE 7

The procedure of example 1 was repeated except that the only adjuvant tested was cyclopentadecanone at concentrations of 0.5, 1, 2, 3, 5 and 10% w/v. From 0.2 to 0.9 ml of methanol was added to 2.7 ml of the solution to help dissolve the ketone in the propylene glycol at higher concentrations. The presence of methanol did not appreciably change the permeability of the skin as demonstrated by the profile obtained with the control sample containing methanol. Based on graphing the data, it was observed that the minimal effective concentration of the adjuvant was 2%.

Based upon such graphing, the rates of flux calculated from the linear portion of the curve are given in Table 6.

TABLE 6

| Concentration of Adjuvant | Flux (dpm/cm²/hr) | Ratio (%) |
|---|---|---|
| 10 | $7.4 \times 10^3$ | 4625 |
| 5 | $4.1 \times 10^3$ | 2563 |
| 3 | $3.7 \times 10^3$ | 2310 |
| 2 | $3.7 \times 10^3$ | 2310 |
| 1 | $0.31 \times 10^3$ | 200 |
| 0.5 | $0.31 \times 10^3$ | 100 |
| 0 (Control) | $0.16 \times 10^3$ | 100 |

Studies with Oxacyclohexadecan-2-one or cyclopentadeconolide

EXAMPLE 8

Solution

Sample preparation, permeation study and data analysis were carried out using the same procedures as Example 1. The drug used is triamcinolone acetonide and the concentration of cyclopentadeconaolide is 2%.

Work was also done to show the permeation profiles of tritiated triamcinolone acetonide with cyclopentadeconolide. Without the addition of cyclopentadecanolide, no penetrated drug was detected in the receptor compartment. However, when cyclopentadecanolide was used at the level of 2%, the drug, triamcinolone acetonide penetrated through hairless mouse skin. From the permeation profile, four permeation parameters, i.e., lag time, permeability coefficient of membrane (Kp), diffusion constant within membrane (D), and partition coefficient between membrane and vehicle (Km) were analyzed and listed in Table 7.

TABLE 7

Triamcinolone acetone penetration parameters with and without cyclopentadecanolide

| Enhancer | Lag time (hr) | KP (cm/hr) | D (cm²/hr) | Km |
|---|---|---|---|---|
| None | — | — | — | — |
| cyclopenta-decanolide (2%) | 6.03 | 3.88 | $4.42 \times 10^{-7}$ | $3.51 \times 10^4$ |

EXAMPLE 9

Cream

In a separate set of experiments, the formulations were of aqueous emulsion of cyclopentadeconolide in saline or buffer with Tween 20 as an emulsification agent. Cyclopentadecanolide in the desired amount was combined with Tween 20 and saline, in a 40° C. water bath/sonicator and emulsified by sonication. In this set of experiments the enhancement of hydrocortisone penetration through hairless mouse and human cadaver skin was examined. The range of cylcopentadeconolide concentration was 0.001–10%. A predetermined concentration of enhancer was combined with radio-labelled tritiated hydrocortisone in saline at a concentration of 0.05 mM. Tween 20 (1 or 0.1%) was placed in the donor compartments to emulsify the enhancer. The receiver compartments were filled with saline.

Work was also done to show the effect of cyclopentadeconolide on hydrocortisone permeation as a function of enhancer concentration. Studies with hairless mouse skin were done in which the concentration of cyclopentadeconolide spanned 0.001% to 10%. Enhancement of hydrocortisone transport was detected as low as 0.001%, although the difference from the permeability of the controls was not significantly different at the 90% confidence level. The enhancement ratio was greatest at 1% cyclopentadecanolide. A similar concentrational dependency study was done with human cadaver skin. Significant (with 90% confidence) enhancement was detected at 0.003% cyclopentadecanolide with maximum enhancement occurring at 0.32% and 3.2% cyclopentadecanolide. For both hairless mouse and human cadaver skin, the magnitude of enhancement ranged from about 2 to 10; furthermore, it appeared that both skin types were comparably sensitive to cyclopentadecanolide effect.

Spray

The illustration, previously shown in Example 2, explains the use of cylclopentadecanolide in the nasal spray of insulin for the reduction of blood glucose in dogs. Similarly, Example 3 illustrates that cyclopentadecanolide can be used in the nasal spray formulations for the treatment of Type II diabetes in humans.

EXAMPLE 10

Civetone, 9-Cycloheptadecen-1-One

Sample preparation, permeation study and data analysis were carried out following the procedure referred to in Example 1. The enhancer used in this study is civetone at the level of 2% in the solution of donor compartment of diffusion cell.

Work was done to show the permeation profile of triatiated triamcinolone acetonide through hairless mouse skin with and without civetone. Based upon graphing the data which was collected, the steady-rate permeation rate, calculated from the slope of permeation profile, was $8.36 \times 10^{-3}$ ug/cm *cm/hr with civetone; while it is only $1.10 \times 10^{-3}$ ug/cm *cm/hr without civetone. There was a 760% increase in the percutaneous permeation rate of triamcinolone acetonide when civetone was used as skin enhance; at the level of 2%.

EXAMPLE 11

Ethylene Brassylate or Ethylene Undecane Dicarbosylate

The preparation of skin permeation study, and data analysis follow the methods illustrated in Example 1, except that the drug used is propranolol HCl and the permeation enhance; used is ethylene brassylate at the 10% concentration. The permeation rate of tritiated propranolol HCl through hairless mouse skin enhanced with 10% ethylene brassylate is 15.8 ug/cm *cm/hr, while the permeation rate of tritiated propranolol without enhance; is 5.05 ug/cm *cm/hr. There is a 3-fold increase in steady state permeation rate when ethylene brassylate is added. Simultaneously, 5% cyclopentadecanolide is used as a positive control. The steady state permeation rate is 24.8 ug/cm *cm/hr, a 5-fold increase. The text data was graphed to show the penetration profile of tritiated propranolol HCl enhanced by ethylene brassylate and cyclopentadecanolide, respectively. Table 8 lists the penetration parameters i.e. lag time, partition coefficient for the vehicle to the membrane, diffusion coefficient, and permeability coefficient within the membrane analyzed from the penetration profile presented in the graphed data.

therapeutic agents. These include anti-hypertensive drugs such as clonidine and propranolol, anti-sedative drugs such as diazepam, steroidal hormones such as estradiol, steroidal anti-inflammatory drugs such as glucocorticoids, hydrocortisone, or triamcinolone acetonide, non-steroid anti-inflammatory drugs such as indomethacin, anti-psoriasis drugs such as psoralen, calcium blockers such as verapramil, anti-diabetic drugs such as insulin, estrus synchronizing agent such as progestin, contraceptives such as estradiol, and so on. Other types of drugs whose rate of transdermal or transmembrane passage would be increased include, but not limited to, antibiotics, antifungal agents, CNS depressants, and sunscreens.

EXAMPLE 13

Percutaneous Absorption of Triamcinadone Acetonide

The procedure of example-1 was repeated except that 3-methyl-cyclopentadecanone was used as the adjuvant and 0.1 to 0.3 ml ethanol was added to the solution to completely dissolve the adjuvant. This amount of ethanol did not appreciably change the permeability of the skin as demonstrated by the profiles of the controls with and without ethanol. The penetration profiles were obtained by graphing the text data. Graphing showed that the minimal effective concentration of the adjuvant is 2%.

The rates of flux calculated from the linear portions of the curves of the graphed data are given in Table 9.

TABLE 8

PERMEATION PARAMETERS OF PROPRANOLOL

|  | T hr | Kp cm/hr | D cm*cm/hr | Km |
|---|---|---|---|---|
| Control | 2.06E + 00 | 1.17E − 02 | 1.29E − 06 | 3.63E + 01 |
| 10% V/V Ethylene Brassylate | 1.80E + 00 | 3.68E − 02 | 1.48E − 06 | 9.95E + 01 |
| 5% W/V Cyclopentadecanolide ENHANCER | 7.20E − 01 | 5.75E − 02 | 3.70E − 06 | 6.21E + 01 |

EXAMPLE 12

In a separate study, a cream formulation containing tritiated hydrocortisone and ethylene brassylate was used. The content of the formulation was the same as Example 9, except for the replacement of the enhancer. The enhancement ratio of hydrocortisone by 3-methyl cyclopentadecanone and ethylene brassylate as a function of skin type was calculated from the test data. It shows that percutaneous absorption of hydrocortisone can be enhanced by a 5.5-fold and 2.5-fold increase with 10% 3-methyl cyclopentadecanone and 10% ethylene brassylate respectively. The results obtained from examples 6 to 12 clearly indicate that macrocyclic compounds including macrocyclic ketones with or without alkyl group, macrocyclic lactones, and polyesters of ethyelene and dicarboxylic acids, possess the property of enhancing the rate of passage of drugs through skin, nasal membranes, and other biological membranes.

Types of Therapeutic Drugs

Examples 13 to 20 illustrate the uses of macrocyclic compounds as permeation enhancers for different types of

TABLE 9

| Concentration % | Flux (dpm/cm²/hr) | Ratio (%) |
|---|---|---|
| 10 | 0.3 × 10³ | 3000 |
| 5 | 0.3 × 10³ | 3000 |
| 3 | 0.22 × 10³ | 2200 |
| 2 | 0.15 × 10³ | 1500 |
| 1 | 0.10 × 10³ | 1000 |
| 0.5 | 0.013 × 10³ | 130 |
| 0% (with ethanol) | 0.025 × 10³ | 250 |
| 0% (no ethanol) | 0.010 × 10³ | 100 |

EXAMPLE 14

Percutaneous Absorption of Psoralen

The procedure of example 1 was repeated except that the drug was 8-methoxy-psoralen (MOP) with a concentration of 46 mg/ml used as $H^3$-MOP dissolved in propylene glycol, and the adjuvants tested were 3-methylcyclopentadecanone (I) (0.4% w/v) and cycloundecanone (III) (2% w/v). The test data was graphed to show the penetration profiles.

The rates of flux calculated from the lines portion of the curves of the graphed data are shown in Table 10.

TABLE 10

| Adjuvant | Flux (dpm/cm²/hr) | Ratio (%) |
| --- | --- | --- |
| Control | $1.88 \times 10^3$ | 100 |
| 0.4% I | $8.13 \times 10^3$ | 432 |
| 2% III | $3.63 \times 10^3$ | 193 |

EXAMPLE 15

Percutaneous Absorbtion of Clonidine

The process of example 1 was repeated except that tritiated clonidine, diluted 1000 fold with cold clonidine was used. The tests were run with a propylene glycol containing 37.4 mg/ml clonidine and 2% (w/v) cyclopentadecanone. The test data was graphed to show the penetration profiles. Based on the profile the flux of the preparation containing the adjuvant was 10.1 mg/cm²/hr or equivalent to $1.83 \times 10^6$ dpm/cm²/hr of the respective radioisotopically labeled drug.

EXAMPLE 16

Percutaneous Absorption of Diazepam

The procedure of example 15 was repeated except that $^{14}$C diazepam, diluted 100 fold with cold diazepam, was used. The tests were run with a propylene glycol solution containing 1.91 mg/ml of diazepam and 2% (w/v) cyclopentadecanone. The test data was graphed to show the penetration profiles.

EXAMPLE 17

Percutaneous Absorption Diazepam

The procedure of example 15 was repeated except that 14 C diazepam, diluted 1,000 fold with cold diazepam, was used. The propylene glycol solution contained 18.9 mg/ml of diazepam and 2% (w/v) of cyclopentadecanone.

EXAMPLE 18

Percutaneous Absorption of Estradiol

The procedure of example 15 was repeated except that 14 C estradiol, diluted 100 fold with cold estradiol, was used. The tests were run with a propylene glycol solution containing 1.06 mg/ml estradiol and 2% (w/v) cyclopentadecanone.

EXAMPLE 19

Percutaneous Absorption of Propranolol

The procedure of example 15 was repeated except that tritiated propranolol diluted 100 fold with cold propranolol, was used. The tests were run with a propylene glycol solution containing $9.7 \times 10^{-3}$ mg/ml propranolol and 2% (w/v) cyclopentadecanone.

EXAMPLE 20

Percutaneous Absorption of Verapramil

The procedure of example 15 was repeated except that tritiated verapramil, diluted 1000 fold with cold verapramil, was used. The tests were run with a propylene glycol solution containing $1.54 \times 10^{-2}$ mg/ml verapramil and 2% (w/v) cyclopentadecanone.

Examples 21 and 22 relate to the use of enhancers in drug compositions that are applied using a transdermal patch or similar delivery system. In particular, studies were conducted with respect to the compatibility of the enhancers with polymers used in these patches, such as silastic elastomers or pressure sensitive adhesives made by Dow Corning Corporation, Midland, Mich. The methods of evaluation are described below:

A. Preparation of adhesives solution

The appropriate quantity of adhesive solution was weighed and added to a known weight of cyclopentadecanone so as to provide results in the 0, 1, 5, 20 or 30 wt % (w/w of cyclopentadecanone (permeation enhancer) in the dry adhesive 100% solids) following coating.

B. Machine Coating Laminates

The adhesive solution was coated onto Scotchpak 1022 release liner (manufactured by 3M Company, St. Paul, Minn.) with a custom fabricated Meyer bar (40 threads/inch, depth 0.003") at a speed of 165 inches/minute with a setting of 5.5 on the motor scale, onto release liner (2 mil thick) and allowed to air dry for a minimum of 30 minutes. The base was cleaned with Freon PCA following coating of the adhesive solution. The cast adhesive was allowed to dry at room temperature to allow the Freon PCA to evaporate. A sheet of polyester was then transfer-coated using IPA and a squeeze, then a 4.5 lb rubber roller. These resulted in a 1 and 2 mil thick layer of 355 BIO-PSA(R) Medical Grade Adhesive and X-7-2920 BIO-PSA(R) Amine Resistant Medical Grade Adhesive, respectively.

C. Testing of Laminates

The tape properties of laminates were tested initially (after a minimum of 24 hours after preparation) or after two weeks of aging at room temperature (20 to 25 degree C.).

D. Measurement of Tape Properties

D.1. Surface tack measurement

Pressure sensitive adhesives have the ability to form a bond with another surface during a short contact time under low pressure. This general phenomenon is known as tack or quick stick. The strength of the bond depends upon the application pressure, dwell time, and the rate of withdrawal. Quantitative tack measurements were performed through use of a Polyken (Tm) brand Probe Tack Tester (Testing Machines, Inc. Amityville, N.Y.). Briefly summarized, tack measurements, expressivity of 0.5 cm/sec., a contact pressure of 100 grams/cm2, and contact time of 0.5 cm/seconds. The method is based on ASTM D-2979. Adhesive laminates were cut into 2.5 cm×2.5 cm pieces. A test sample was placed on the tester with the "donut" shaped weight on top of it. The maximum force was recorded (n=5) for replicate samples. The probe was wiped with a lint-free material dipped in acetone after each series of five pieces. The probe was allowed to stand for at least 2 seconds after being wiped with a dry cloth to air dry. The average of these readings and the standard deviation were reported.

D.2. Peel/Release Adhesion (Peel Force)

The resistance of an adhesive tape to a peeling force is known as the peel adhesion or the release. The peel values reported were obtained in a manner similar to that used to test adhesion. Adhesive laminates were prepared and cut into one-inch wide strip of laminated release liner (SCOTCHPAK(R) 1002(R), adhesive, and MYLAR(R) polyester film). The release liner was stripped at a rate of 40 inches/minute at an angle of 180 degrees while attached to a tensile testing machine, with the results expressed in grams per centimeter. An average value over the entire panel was recorded. Data were expressed as the mean +/– SD (n=3).

D.3. Adhesion Force

The adhesion force with respect to a stainless steel test panel was determined. Quantitative adhesion measurements reported were obtained through use of a one-inch wide MYLAR(R) polyester tape coated with a layer of adhesive. The tape was adhered to a stainless steel panel with a 4.5 lb. roller and stripped attached to a tensile testing machine, with the results expressed in grams per centimeter. Between each run, test panels were cleaned with acetone and trichloroethylene and allowed to air dry. Data were expressed as the mean +/– S.D. (n=3) unless otherwise specified.

D.4 Interpretation of Tape Property Tests

An arbitrary minimum value for tack (>50 g/cm2) and adhesion, (>200 g/cm) and maximum value for peel<50 g/cm were used as a criterion to determine the suitability of tape properties of the test samples for use in a transdermal drug delivery system.

EXAMPLE 21

The purpose of this study was to determine the compatibility of cyclopentadecanone (0, 1, 5, and 10 wt %), a skin penetration enhancer in comparison with other selected enhancers including: Azone (R), ethanol, isopropyl myristate, isopropyl palmitate, and eucalyptol, on the tape properties (i.e. peel, subsequent adhesion, and tack) of 355 BIO-PSA(R) and x7-2920 Amine Resistant BIO-PSA(R) Medical. Grade Silicone Pressure Sensitive Adhesives and the effect of these enhancers on tape properties were evaluated initially under various aging conditions.

355 BIO-PSA(R) has been used and x7-2920 Amine Resistant BIO-PSA(R), has been developed for use in transdermal drug delivery system and reported by Huie, Schmidt, and Warren in Testing Adhesive and Liner for Transdermal Drug Delivery, Adhesive Age, June issue 1985 and also by Krug and Marecki in Porous and Other Medical Pressure Sensitive Adhesives, Adhesives Age, November issue page 19–23, 1983.

Tables 11 to 13 illustrated the use o enhancers in the transdermal drug delivery systems and the effect of loading on the initial tape properties. The cyclopentadecanone was soluble in the adhesive prior to casting. Laminates containing 10 wt % cyclopentadecanone were clear. Slight and mark crystallization were observed in laminates containing 20 and 30 wt % cyclopentadecanone indicating that the level of solubility of cyclopentadecanone in 355 adhesive solids was between 10–20 wt %.

The tack and tape properties of the 10 wt % cyclopentadecanone laminates were similar to 355 control laminates. The compatibility of 0, 1, 5, and 10 wt % levels of cyclopentadecanone in comparison with other enhancers on the initial tape properties of DC 355 pressure sensitive adhesive (PSA) are shown in TABLE 11. The initial peel force of all laminates containing up to 10 wt % of each enhancer was low (<10 g/cm) and acceptable for a transdermal drug delivery system. Cyclopentadecanone was found to increase the peel force, and reduce adhesion proportional to its loading level in both DC 355 and X7-2920 pressure sensitive adhesives. A maximum loading level of 10 wt % cyclopentadecanone was considered to be compatible with both DC 355 (TABLE 11) and x7-2920 BIO-PSA(R) (TABLES 12 & 13).

Ethanol did not adversely affect tape properties of either DC 355 (TABLE 11) or X7-2920 BIO-PSA (TABLES 12 & 13) at levels of 10 wt %; however, the low alcohol most likely evaporated due from time of tape preparation to time of testing. The concentrations of ethanol in the tested tape probably are negligible.

Azone(R), isopropyl palmitate, and isopropyl myristate appeared to be soluble in both PSA's at levels of 10 wt %; however, they plasticized the adhesive resulting in cohesive failure (i.e. transfer of adhesive to release liner, leaving residue after peel, residue on adhesion test panels, and acted as a solvent for the adhesives).

The maximum compatible levels of these enhancers with both 355 and X7-2920 BIO-PSA(R) were isopropyl palmitate (1 wt %), isopropyl myristate (5 wt %), Azone (R) (1–2 wt %), eucalpyptol (<5 wt %).

In short, cyclopentadecanone can be incorporated into silicone pressure sensitive adhesives at higher levels than other penetration enhancers without compromising tape properties and thus, can be considered for use in drug/silicone adhesive matrix or laminate transdermal drug delivery systems.

EXAMPLE 22

Aging studies were carried out on laminates of DC 355 BIO PSA(R) with each enhancer. The effect of 1 wt % loading levels of cyclopentadecanone, Azone(R), ethanol, isopropyl myristate, isopropyl palmitate, and eucalyptol on initial tape properties of DC 355 machine coated laminates are shown in TABLE 14. The effect of these enhancers on tape properties of DC 355 after two weeks of aging are shown in TABLE 15. The tack, peel, and adhesion value for the control DC 355 laminates were reduced by 71, 509, and 5 percent, respectively from initial values TABLE 14 vs. TABLE 15). Noted is that after two weeks of aging only cyclopentadecanone increases the adhesion; while other decrease the adhesion (TABLE 15).

Examples 21 and 22 illustrate the tape properties resulted from the studies on the compatibility of cyclopentadecanone with silicone pressure sensitive adhesives. Cyclopentadecanone was found to increase the peel force, and reduce adhesion proportional to its loading level in both DC 355 and X7-2920 pressure sensitive adhesives. A maximum loading level of 10 wt % cyclopentadecanone was considered to be compatible with both DC 355 and x7-2920 BIO-PSA(R). Data obtained from a comparative study shows that the maximum compatible levels of other permeation enhancers with both 355 and x7-2920 BIO-PSA(R) were isopropyl palmitate (1 wt %), eucalyptol (<5 wt %). In conclusion, cyclopentadecanone can be incorporated into silicone pressure sensitive adhesives at higher levels than other enhancers and thus, can be considered for use in drug/silicone adhesive matrix or transdermal drug delivery systems.

TABLE 11

Effect of Skin Penetration Enhancers on Tape Properties of 355 Pressure Sensitive Adhesive

| Skin Enhancer | Loading Wt % | Initial Tape Properties[a] | | |
|---|---|---|---|---|
| | | Tack (g/cm2) | Peel (g/cm) | Adhesion (g/cm) |
| Control | 0 | 92.0 | 1+/–0.2 | 290.0 |
| CIB-01 (cyclopenta decanone) | 1 | 358.0 | 1.8 | 342.0 |
| | 5 | 624.0 | 7.3 | 256.3 |
| | 10 | 780.7 | 9.1 | 193.7 |
| Ethanol[b] | 1 | 119.7 | 1.1 | 269.3 |
| | 5 | 239.0 | 1.4 | 263.0 |
| | 10 | 314.3 | 1.1 | 305.5 |
| Isopropyl Palmitate | 1 | 407.3 | 3.5 | 506.6 |
| | 5 | 864.0 | 9.1 | 172.6* |
| | 10 | 284.0 | 3.9 | 58.7** |

TABLE 11-continued

Effect of Skin Penetration Enhancers on Tape Properties of 355 Pressure Sensitive Adhesive

| Skin Enhancer | Loading Wt % | Initial Tape Properties[a] | | |
|---|---|---|---|---|
| | | Tack (g/cm2) | Peel (g/cm) | Adhesion (g/cm) |
| Azone (R) | 1 | 357.6 | 1.4 | 290.4 |
| | 5 | 212.7 | 2.5 | 322.7** |
| | 10 | 113.3 | 2.5 | 389.9** |

[a]Samples were hand-coated with a No. 8 coating bar. Severe compromise of tape properties (*), cohesive failure (**).
[b]Ethanol was very volatile and vaporized out during preparations. The final concentration of ethanol remaining in the patch was not able to be determined.

TABLE 12

Effect of Skin Penetration Enhancers on Tape Properties of X7-2920 Amine Resistant Pressure Sensitive Adhesive

| Skin Enhancer | Loading Wt % | Initial Tape Properties[a] | | |
|---|---|---|---|---|
| | | Tack (g/cm2) | Peel (g/cm) | Adhesion (g/cm) |
| Control | 0 | 612.7 | 11.8 | 1170.0 |
| CIB-01 (cyclopenta-decanone) | 1 | 573.3 | 8.4 | 831.0 |
| | 5 | 598.0 | 11.6 | 2124.0 |
| | 10 | 915.3 | 15.5 | 2137.0 |
| Ethanol[b] | 1 | 246.3 | 3.5 | — |
| | 5 | 297.0 | 4.2 | 967.6 |
| | 10 | 288.3 | 5.6 | 960.1 |
| Isopropyl Palmitate | 1 | 385.3 | 6.3 | 204.5 |
| | 5 | 712.0 | 10.9 | 204.5 |
| | 10 | 524.7 | 14.1 | 290.7** |
| Azone (R) | 1 | 312.0 | 1.8 | 1509.0 |
| | 5 | 703.0 | 16.9 | 1238.0** |
| | 10 | 714.3 | 22.9 | 1424.0** |

[a]Samples were hand-coated with a No. 8 coating bar. Severe compromise of tape properties, cohesive failure (**).
[b]Ethanol was very volatile and vaporized out during fabrication. The final concentration of ethanol remaining in the patch was not able to be determined.

TABLE 13

Effect of Skin Penetration Enhancers on Tape Properties of X7-2920 Amine Resistant Pressure Sensitive Adhesive

| Skin Enhancer | Loading Wt % | Initial Tape Properties[a] | | |
|---|---|---|---|---|
| | | Tack (g/cm2) | Peel (g/cm) | Adhesion (g/cm) |
| Control | 0 | 115.0 | 0.7+/−0.9 | 720+/−38 |
| CIB-01 (cyclopenta-decanone) | 1 | 105.0 | 0.2+/−0.2 | 681+/−16 |
| | 5 | 403.0 | 7.0+/−1.4 | 623+/−29 |
| | 10 | 857.0 | 0.7+/−0.4 | 698+/−12 |
| Ethanol[b] | 1 | 84.0 | 1.0+/−0.4 | 697+/−10 |
| | 5 | 72.0 | 1.4+/−0.7 | 736+/−31 |
| | 10 | 60.0 | 18.9+/−1.1 | 477+/−50 |
| Isopropyl Palmitate | 1 | 171.0 | 1.8+/−0.4 | 639+/−38 |
| | 5 | 845.0 | 18.6+/−1.4 | 400+/−71 |
| | 10 | 758.0 | 17.2+/−2.8 | 445+/−91** |
| Azone (R) | 1 | 758.0 | 1.4+/−0.4 | 716+/−46 |
| | 5 | 535.0 | 7.0+/−1.4 | 723+/−57 |
| | 10 | 706.0 | 22.9+/−4.2 | 320+/−42** |

[a]Machine-coated samples. Severe compromise of tape properties, cohesive failure (**).
[b]Ethanol was very volatile and vaporized out during fabrication. The final concentration of ethanol remaining in the patch can not be determined.

TABLE 14

Compatibility of Skin Penetration Enhancers with DOW CORNING(R) 355 Medical Grade Pressure Sensitive Silicone Adhesive

| Skin Enhancer | Loading Wt % | Initial Tape Properties, Mean ± SD | | | | | |
|---|---|---|---|---|---|---|---|
| | | Tack (g/cm2) | %[a] | Peel (g/cm) | %[a] | Adhesion (g/cm) | %[a] |
| Control | 0 | 187.0 | — | 1.4 ± 0.0 | — | 466.1 ± 17.9 | — |
| CIB-Ol[b] | 1 | 339.0 | +81 | 2.8 ± 0.0 | +100 | 458.1 ± 17.9 | −2 |
| Azone | 1 | 114.7 | −38 | 2.8 ± 0.4 | +100 | 502.4 ± 66.1 | +8 |
| Ethanol | 1 | 134.3 | −28 | 1.4 ± 1.0 | +0 | 554.0 ± 23.6 | +18 |
| Isopropyl Myristate | 1 | 295.3 | +58 | 7.4 ± 0.7 | +21 | 486.2 ± 27.8 | +4 |
| Isopropyl Palmitate | 1 | 229.3 | +22 | 6.3 ± 0.7 | +350 | 536.8 ± 32.0 | +15 |
| Eucalyptol | 1 | 158.7 | −15 | 1.4 ± 1.1 | +0 | 465.4 ± 23.6 | −2 |

[a]Percent change from control values for machine-coated laminates 1 mil thick.
[b]CIB-Ol is cyclopentadecanone.

TABLE 15

Compatibility of Skin Penetration Enhancers with DOW CORNING(R) 355 Medical Grade Pressure Sensitive Silicone Adhesive

| Skin Enhancer | Loading Wt % | Tape Properties, Mean ± SD After Two Weeks Aging | | | | | |
|---|---|---|---|---|---|---|---|
| | | Tack | %[a] | Peel | %[a] | Adhesion | %[a] |
| Control | 0 | 53.0 | −71 | 0.7 ± 0.0 | −50 | 444.0 ± 4.9 | −5 |
| CIB-Ol[b] | 1 | 103.0 | −70 | 1.4 ± 0.3 | +50 | 515.7 ± 32.6 | +13 |
| Azone | 1 | 90.0 | −22 | 1.8 ± 0.4 | +36 | 483.0 ± 19.3 | −4 |
| Ethanol | 1 | 48.7* | −63 | 2.1 ± 0.4 | +50 | 525.6 ± 3.2 | −5 |
| Isopropyl Myristate | 1 | 185.7 | −37 | 3.9 ± 0.7 | −47 | 428.5 ± 78.4 | −12 |
| Isopropyl Palmitate | 1 | 167.3 | −27 | 8.1 ± — | +30 | 414.1 ± 60.8 | +23 |
| Eucalyptol | 1 | 41.0* | −74 | 0.4 ± 0.7 | −71 | 416.6 ± 95.9 | −10 |

[a]Percent change in the tape properties from initial for 1 mil thick machine-coated laminates. Severe compromise in tape properties. (*)
[b]CIC-Ol is cyclopentadecanone The following examples illustrate other types of compositions which are also suitable. In these examples, the amounts are given in percent by weight.

EXAMPLE 23

The following lotion formulation containing from about 0.001 to 1% by weight of estradiol may be prepared:

| Estradiol | 0.001–1 |
|---|---|
| Cetylalcohol | 15 |
| Propyleneglycol | 10 |
| Sodium lauryl sulfate | 15 |
| Cyclopentadecanone | 2 |
| Water | q.s. 100 |

The next two examples (Nos. 24 and 25) are illustrative of compositions which include an antifungal agent, namely clotrimazole. Evaluations have shown that the presence of the enhancer in the "antifungal" composition improves the topically delivery of the antifungal agent into the epidermis and dermis. Clotrimazole is a broad-spectrum antifungal agent that is used for the treatment of dermal infections caused by various species of pathogenic dermatophytes, yeasts, and *Malassezia furfur*. The primary action of clotrimazole is against dividing and growing organisms. It is used to treat superficial dermatophyte infections, athlete's foot (tinea pedis), jock itch (tinia cruris) and ringworm (tinea corporis due to *Trichophyton rubrum, Trichophyton mentagrophytes, Epidermophyton floccosum*, and *Microsporum canis*). It is also used to treat recurrent vaginal yeast (Candida) infections due to *Candida albicans* and topical candidiasis due to *Candida albicans* and tinea versicolor due to *Malassezia furfur.*

EXAMPLE 24

The following cream formulation containing clotrimazole, an antifungal agent, may be prepared.

| Mineral oil | 31 |
|---|---|
| Cyclopentadecanone | 2 |
| Clotrimazole | 1 |
| Spermaceti | 10 |
| Glycerol monstearate | 10 |
| Paraffin | 8 |
| Water | |

The antifungal composition of Example 25 below is in the form of a gel.

EXAMPLE 25

| Clotrimazole | 1.0% w/w |
|---|---|
| Cyclopentadecanolide | 4.0 |
| Ethanol | 30.0 |
| Glycerin (Glycerol) | 15.0 |
| Propylene Glycol | 30.0 |
| Carbomer 940 | 1.5 |
| Trolamine (Triethanolamine) | 1.0 |
| Water | QS |
| Total | 100.0% w/w |

The following suppository containing an antiseptic, benzethonium chloride, may be prepared.

EXAMPLE 26

| Benzethonium chloride | 2 |
|---|---|
| Cyclopentadecanone | 2 |
| Cocoa butter | 80 |
| Tween 61* | 16 |

*Polyethylene-4-sorbitan monostearate The following film containing procaine hydrocholoride may be prepared.

EXAMPLE 27

| Procaine hydrocholoride | 0.562 |
|---|---|
| Cyclopentadecanone | 2 |
| Polyvinyl alcohol | 30 |
| Polyvinylpyrrolidone | 30 |
| Polyethylene glycol | q.s. 100 |

Following the above procedures, but using those compounds where X is sulfur or imino of the structure =

and when Y is oxygen, sulfur or imino of the structure =NH, similar results of the enhancement of passage of drugs across body membranes were obtained. So, it can be concluded that these cyclic amides, cyclic amidines, cyclic thioesters, cyclic dithioesters and cyclic thioamides are effective as enhancers.

An embodiment of the present invention comprises a composition which is effective in enhancing the qualities of skin and which comprises: (A) a skin-treating compound; (B) an enhancer which is a compound of Formula I above; (C) a carrier; and optionally (D) a cosmetic additive. The term "skin-treating compound" means a material which is effective in enhancing one or more properties of skin as evidenced by statistically significant differences between the quality of untreated skin and skin treated with said material, at the 95% level of confidence, using standard methods of evaluation which are known to persons skilled in the art. Examples of skin characteristics or properties that are capable of being improved by a skin-treating compound include: (A) smoothness of the skin; (B) thickness of the epidermal layer of the skin; (C) increase in the cellular density of the skin; (D) reduction in the depth of interossei; (E) elasticity of the skin; and (F) texture of the skin. Methods for evaluating in an objective way skin properties of the aforementioned type are well known to persons skilled in the art. They include, for example, the use of clinical assessments, photographic assessments, silastic castings, ultra-sound evaluation, histological examination, punch biopsies, and tape stripping.

Examples of classes of materials for use as skin-treating compounds in the practice of the present invention include nutrients, modifiers, rejuvinators, hormones, regulators, immunomodulators, moisturizers, and stimulators. Examples of skin-treating materials for use in the practice of the present invention include: nutrients—vitamins, amino acids, and carbohydrates; modifiers—melanin and antioxidants; rejuvinators—growth factors and human growth hormones; hormones—estrogens, progesterones and other steroids, and growth hormones; regulators—peptides, proteins, and anti-sense variations; immunomodulators—beta 1, 3-glucan and farnesol; moisturizers—vegetable oils, beeswax, and other waxes, lanolins, fatty acid esters, mineral oils, and other hydrophobic materials; and stimulators—tocopheryl nicotinate, retinoids, and alpha-hydroxy acids. A plurality of skin-treating compounds can be used in the composition.

The minimum percent improvement which is imparted by the skin-treating compound(s) to the skin and which constitutes a statistically significant difference, as referred to hereinabove, will vary depending on the skin property being evaluated, as well as on sample size and distribution. For example, in evaluating epidermal thickness, an improvement of 10% or greater is considered by persons skilled in the art as a statistically significant difference. On the other hand, in evaluating elasticity of skin, an improvement of at least about 30% would be considered by persons skilled in the art as constituting a statistically significant difference.

The skin-treating compound(s) is used in conjunction with an enhancer which is a compound within the scope of Formula I above. A plurality of enhancers can be used. Additional improvements in the qualities of the skin are achieved by the use of the enhancer(s) in combination with the skin-treating compound. Such improvements are identified and evaluated by use of the same type of methodologies referred to hereinabove in connection with the skin-treating compound(s). Preferred enhancers for use of the practice of the present invention include macrocylcic ketones and lactones of Formula I above. A particularly preferred enhancer is cyclopentadecanolide.

The skin-treating compound or a mixture of skin-treating compounds should be used in an amount which is effective in improving the quality of the skin. The minimum amount (s) needed to achieve the improvement will vary depending on the particular skin-treating compound or mixture of skin-treating compounds that are used. Generally speaking, it is believed that the skin-treating compound(s) will comprise at least about 0.01 wt. % of the composition. Typically, the skin-treating compound(s) will comprise about 0.1 to about 10 wt. % of the composition. Preferably, the skin-treating compound(s) will comprise about 0.5 to about 3 wt. % of the composition.

The enhancer or a mixture of enhancers can be used in an amount at least effective to impart additional improvements to the skin, that is, improvements beyond those provided by the skin-treating compound. It is believed that, for most applications, the enhancer will comprise about 0.1 to about 30 wt. % of the composition, with a preferred range of enhancer being about 0.5 to about 10 wt. %, and a particularly preferred range comprising about 2 to about 5 wt. % of the composition.

The skin-improving composition of the present invention will generally include also a carrier in which the other ingredients comprising the composition are either dissolved or dispersed in the form of solid particles or liquid droplets. Any suitable material can be used as the carrier, for example, materials which are suitable for use in pharmaceutical and cosmetic compositions. Examples of carriers include water, alcohol, glycerine, sorbitol, propylene glycol, vegetable— and animal-derived oils, waxes, acids, alcohols, esters, ethers, amides, ethoxylates and propoxylates, ethylene and propylene glycol ethers, mineral oils and waxes, silicone oils and waxes, and surfactants. The carrier can comprise one or more compounds. Speaking generally, the carrier will comprise about 10 to about 95 wt. % of the composition.

Optionally, but typically, the composition will include also one or more compounds which impart other desired properties to the composition. Such compounds will typically comprise materials of the type that are used as additives in cosmetic compositions. Examples of such materials are fragrances, colorants, including pigments or dyes, preservatives, thickening agents, pH controlling agents, stabilizers, surfactants, and emulsifiers.

The form of the composition can be liquid, semi-solid, or solid. The composition can be formulated so that it can be dispersed from an aerosol container. For convenience and ease of application, the use of the composition in a cream or lotion form is recommended.

The skin-improving composition can be applied to the skin as often as needed to achieve the desired improvements. The frequency of application will vary depending on the nature of the composition and the involved skin condition. In general, the application of the composition twice a day (for example, in the morning and the evening) will be suitable for treating many conditions and can be continued for as long as is required to obtain the desired results, for example, weeks or months or indefinitely. For some conditions, the composition can be applied every two or three days. In treating the skin of the hands, consideration should be given to applying the composition after every washing.

Compositions for treating hair are also within the scope of the present invention. Such compositions can comprise hair-treating compounds, for example, materials which function as hair conditioners and compounds which improve the manageability of hair. Such compositions can comprise a hair-treating compound and the enhancer of Formula I above, as well as other ingredients, and in amounts as described above in connection with the skin-improving composition.

It should be appreciated also that the enhancer of the present invention can be used to advantage in any type of skin-enhancing composition which includes one or more skin-treating compounds that do not readily or easily penetrate the skin epithelial barrier. Such compositions are well known to those skilled in the art. An exemplary class of such compositions is an anti-oxidant composition. Such compositions typically comprise a variety of natural nutrients, including, for example, vitamins, which function to rejuvenate the skin, retard the signs of aging of the skin and maintain the vitality of skin cells. In an in vivo comparative study involving the use of an anti-oxidant composition within the scope of the present invention and Retin A, a material whose anti-wrinkle property has been well documented, it was determined that the performance of the composition of the present invention was equal to that of Retin A in terms of effecting an increase in epithelial thickness, but without the side effects experienced with Retin A.

The next several examples (Examples 28 to 30) are illustrative of anti-oxidant compositions which promote the natural repair process and retard aging of the skin by providing providing skin cells with beneficial natural nutrients. The enhancer used in the compositions is cyclopentadecanolide. It is believed that the enhancer functions to aid in the delivery of the nutrients effectively to the skin cells for their nourishment. This results in rejuvenation of the skin, imparting to the skin a radiant and youthful appearance. The principal variations among the compositions are related to differences in viscosity and concentrations of ingredients. Such differences illustrate that the compositions can be tailor made for ease and effectiveness of application—for example, for repetitive use during the day, especially after each time the body or parts of the body, such as the hands, are washed or otherwise cleaned, or for application at night prior to sleep.

EXAMPLE 28—HAND AND BODY LOTION

| | |
|---|---|
| Vitamin A Palmitate | 0.38% w/w |
| Magnesium Ascorbyl Phosphate | 0.75 |
| Vitamin E Acetate | 0.38 |
| Alpha-Bisabolol | 0.38 |
| Panthenol (Pantothenyl Alcohol) | 0.25 |
| Edetate Disodium | 0.10 |
| Sodium Citrate | 0.60 |
| Trolamine (Triethanolamine) | 1.70 |
| Diethanolamine Methoxycinnamate (DEA Methoxycinnamate) | 2.00 |
| Aloe Vera Gel Concentrate | 1.00 |
| Beeswax, White | 0.50 |
| Mineral Oil, Light | 4.00 |
| Cetyl Palmitate | 1.00 |
| Soya Sterol | 1.00 |
| Cetyl Alcohol | 2.00 |
| Stearic Acid | 3.00 |
| Carbomer 934 | 0.10 |
| Poly (Vinylpyrrolidone)/1-Eicosene Copolymer | 1.00 |
| Methylparaben | 0.20 |
| Propylparaben | 0.10 |

-continued

| | |
|---|---|
| Imidazolidinyl Urea (Imidurea) | 0.30 |
| Butylated Hydroxytoluene (BHT) | 0.20 |
| Cyclopentadecanolide | 4.00 |
| Fragrance | QS |
| Water | QS |
| Total | 100.00% w/w |

EXAMPLE 29—HAND AND BODY CREAM

| | |
|---|---|
| Vitamin A Palmitate | 0.50 w/w |
| Magnesium Ascorbyl Phosphate | 0.75% |
| Vitamin E Acetate | 1.50 |
| Alpha-Bisabolol | 1.00 |
| Panthenol (Pantothenyl Alcohol) | 1.00 |
| Edetate Disodium | 0.10 |
| Sodium Citrate | 0.60 |
| Trolamine (Triethanolamine) | 0.50 |
| Diethanolamine Methoxycinnamate (DEA Methoxycinnamate) | 2.00 |
| Aloe Vera Gel Concentrate | 1.00 |
| Squalene | 3.00 |
| Cetyl Esters | 2.00 |
| Stearyl Alcohol | 4.00 |
| PEG-40 Stearate | 4.00 |
| Glyceryl Monostearate | 3.00 |
| Methylparaben | 0.20 |
| Propylparaben | 0.10 |
| Imidazolidinyl Urea (Imidurea) | 0.30 |
| Butylated Hydroxytoluene (BHT) | 0.20 |
| Silicone Oils | 5.50 |
| Cyclopentadecanolide | 4.00 |
| Fragrance | QS |
| Water | QS |
| Total | 100.00% w/w |

EXAMPLE 30—NIGHT CREAM

| | |
|---|---|
| Vitamin A Palmitate | 0.375% w/w |
| Magnesium Ascorbyl Phosphate | 3.000 |
| Vitamin E Acetate | 1.500 |
| Alpha-Bisabolol | 1.000 |
| Panthenol (Pantothenyl Alcohol) | 1.000 |
| Edetate Disodium | 0.100 |
| Sodium Citrate | 0.600 |
| Trolamine (Triethanolamine) | 0.500 |
| Diethanolamine Methoxycinnamate (DEA Methoxycinnamate) | 2.000 |
| Aloe Vera Gel Concentrate | 1.000 |
| Squalene | 3.000 |
| Cetyl Esters | 2.000 |
| Mineral Oil, Light | 4.000 |
| Stearyl Alcohol | 4.000 |
| PEG-40 Stearate | 2.500 |
| Glyceryl Monostearate | 4.500 |
| Methylparaben | 0.200 |
| Propylparaben | 0.100 |
| Imidazolidinyl Urea (Imidurea) | 0.300 |
| Butylated Hydroxytoluene (BHT) | 0.200 |
| Silicone Oils | 5.000 |
| Cyclopentadecanolide | 4.000 |
| Fragrance | QS |
| Water | QS |
| Total | 100.00% w/w |

The ingredients of the compositions of Examples 28 to 30 are formulated into a substantially homogeneous composition with standard mixing, stirring, or shearing equipment, for example, at 40°–90° C., to form a creamy emulsion or lotion with a smooth feeling. The resultant compositions can be packaged, as appropriate, in plastic tubes, glass jars, or bottles. The compositions evidence stability even under drastic conditions, for example, at 60° C. for 3 months.

The hand and body cream of Example 29 is evaluated for effectiveness in tests involving humans (15 caucasians, aged 50 years and older). The test subjects use the composition of Example 29 or a placebo cream, according to the blind code, for the first 2 months and then all subjects use the composition of Example 29. The test compositions are rubbed into the hands daily at night before the test subjects retire. The following techniques are used to evaluate the performance of the composition on the back of the hand: (A) photographs; (B) silastic castings; (C) ultrasound B-mode scans; (D) biopsies for histological examination; and (E) ballistometry. The overall effects observed as a result of the use in the evaluations of the composition of Example 29 are summarized hereafter.

On the basis of photographic assessments (A) above, a comparison of the subjects shows a gradual improvement in the appearance of the dorsal surface of the hands as a result of the use of the composition of Example 29. Study of the photographs reveal that there is a decrease in the number of lines, a decrease in the depth of the interossei, and a general improvement in the smoothness of the skin. Use of composition of Example 29 appears to improve both the quality of the stratum corneum and the hydration of the epidermis and dermis. Improvement in the interossei depth, as manifested by a decrease in the depth, would indicate a dermal improvement.

Silastic castings of (B) above are evaluated and compared by two independent scorers. Changes in the skin's topography are rated according to the following scale: positive response; no response or no change; and negative response or worsening. These results are then averaged. At 30 days, there is no significant difference in the skin's topography. At 90 days, the silastic castings show that 60% of the subjects exhibited a positive response in the skin's topography, and at 180 days, 73% of the subjects have a positive response.

On the basis of ultrasound evaluation of (C) above, the overall effects which are produced by use of the composition of Example 29 can be summarized by three observations: (1) the epidermis in most of the subjects becomes thicker and better hydrated; (2) the papillary dermis increases in density; and (3) the reticular dermis increases in density. The time course of events shows a gradual increase in thickness and density to up to three or four months. After this period, the increase reaches a steady state or declines slightly. These findings suggest an initial proliferative effect of the product on the epidermis followed by dermal restructuring.

From histological examination of (D) above, the stained sections are examined and evaluated for the following parameters: (1) epidermal thickness; (2) size of the granular layer; (3) appearance of the stratum corneum; and (4) appearance of the dermis. Epidermal thickness increases by 19% over the course of the study, with a 50% increase being found in epidermal thickness in some subjects. Granular layer increases in all subjects to at least double in thickness. This increase is estimated by the number of granular cells. Stratum corneum appearance is markedly different in most subjects. From a compacted initial appearance, the stratum corneum assumes a basket weave pattern that is associated with a younger epidermis. Dermal evaluation is difficult to assess in that no special stains are used. Overall most subjects will show an increase in cellularity of the dermis. This finding would be consistent with a restructuring process of the dermis.

On the basis of ballistometer evaluation of (E) above, 10 subjects have a positive response and 4 subjects have no significant change. One subject has a negative response.

This test measures dermal changes (not epidermal changes) and suggests that some restructuring of the dermis is occurring.

Based on the data that is obtained in the evaluation of the use of the composition of Example 29, conclusions can be made respecting the use of the composition of Example 29: (1) the product is effective in increasing epidermal thickness; (2) the product is effective in producing a smooth, well structured stratum corneum; (3) the product increases epidermal proliferation; (4) the product increases skin elasticity; (5) the product helps restore the dermal structure; and (6) the product is effective in restoring aging hands to a more youthful appearance.

The next two examples are illustrative of the use of the enhancer of the present invention in sunscreen compositions. Such compositions typically contain a plurality of sunscreen agents which are compounds that function to protect the skin by virtue of their ability to absorb various wavelengths of potentially harmful ultraviolet radiation. Sunscreen compositions should have a combination of properties including, for example: (A) the fundamental ability to absorb the involved radiation; (B) the ability to continue to absorb the radiation over a prolonged period of time; and (C) the ability to resist removal upon exposure to water and/or perspiration. It is known that various sunscreen agents penetrate the skin relatively rapidly, with subsequent loss to lower skin layers (dermis) and eventually to systemic circulation. In the development of the present invention, it has been observed that the sunscreen agent(s) in the composition of the present invention is retained at higher concentrations for longer periods of time in the epidermis. It is believed that concentrating the sunscreen agent in the epidermis helps to provide a natural resistance to removal by exposure to physical contact and to water, including perspiration. The extent of this "retaining" effectiveness is dependent on the particular sunscreen agent(s) and carrier used and the concentration of the enhancer. The enhancer used in each of the compositions of Examples 31 and 32 is cycloentadecanolide.

EXAMPLE 31—SUNSCREEN LOTION

| | |
|---|---|
| Benzophenone-3 (Oxybenzone) | 3.0% w/w |
| Diethanolamine Methoxycinnamate (DEA Methoxycinnamate) | 3.0 |
| Cyclopentadecanolide | 4.0 |
| Silicone Oil | 5.0 |
| Glyceryl Monostearate | 5.0 |
| PEG-40 Stearate | 1.0 |
| Sodium Lauryl Sulfate | 0.5 |
| Stearyl Alcohol | 7.1 |
| Cetyl Esters | 5.0 |
| Propylparaben | 0.2 |
| Butylated Hydroxytoluene (BHT) | 0.2 |
| Diethylene Glycol Monomethyl Ether | 30.0 |
| Water | QS |
| Total | 100.0% w/w |

EXAMPLE 32—SUNSCREEN LOTION

| | |
|---|---|
| Benzophenone-3 (Oxybenzone) | 3.00% w/w |
| Diethanolamine Methoxycinnamate (DEA Methoxycinnamate) | 3.00 |
| Cyclopentadecanolide | 4.00 |
| Silicone Oil | 1.00 |
| Glycerin (Glycerol) | 5.00 |
| Propylene Glycol | 5.00 |

-continued

| | |
|---|---|
| Carbomer 941 | 0.25 |
| Squalane | 3.00 |
| Stearic Acid | 1.50 |
| Cetyl Esters | 0.50 |
| Cetyl Alcohol | 0.50 |
| Glyceryl Monostearate | 3.00 |
| PEG-40 Stearate | 1.50 |
| Trolamine (Triethanolamine) | 0.50 |
| Methylparaben | 0.20 |
| Propylparaben | 0.10 |
| Imidazolidinyl Urea (Imidurea) | 0.30 |
| Fragrance | QS |
| Water | QS |
| Total | 100.00% w/w |

It should be appreciated that the present invention provides an effective means for improving the delivery to the body of a variety of types of materials which have beneficial effects on the body.

I claim:

1. A composition which is effective in enhancing the qualities of skin and which comprises: (A) a skin-treating compound; (B) a compound having the structure:

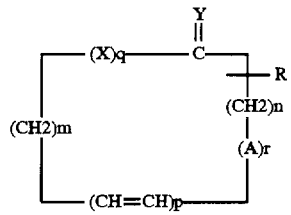

wherein X and Y are oxygen, sulfur or an imino group of the structure=N—R, with the proviso that when Y is an imino group, X is an imino group, and when Y is sulfur, X is sulfur or an imino group, A is a group having the structure

wherein X and Y are as defined above, m and n are integers having a value from 1 to 20 and the sum of m+n is not greater than 25, p is an integer having a value of 0 or 1, q is an integer having a value of 0 or 1, r is an integer having a value of 0 or 1, and R is hydrogen or an alkyl group which has from 1 to 6 carbon atoms and which may be straight chained or branched, with the proviso that when p, q and r are 0 and Y is oxygen, m+n is at least 11; (C) a carrier; and optionally (D) a cosmetic additive.

2. A composition according to claim 1 comprising about 0.1 to about 10 wt. % of said skin-treating compound and about 0.1 to about 30 wt. % of said compound (B).

3. A composition according to claim 2 comprising about 0.5 to about 3 wt. % of said skin-treating compound and about 0.5 to about 10 wt. % of said compound (B).

4. A composition according to claim 3 comprising about 2 to about 5 wt. % of said compound (B).

5. A composition according to claim 2 which is an anti-oxidant composition and wherein the skin-treating compound includes an anti-oxidant material.

6. A composition according to claim 5 wherein said compound of (B) is cyclopentadecanolide.

7. A composition according to claim 2 wherein said compound (B) is cyclopentadecanolide.

* * * * *